US007268253B2

(12) United States Patent
Boehm et al.

(10) Patent No.: US 7,268,253 B2
(45) Date of Patent: Sep. 11, 2007

(54) PROCESS FOR PREPARING α, α-DIALKYL-α-HYDROXYMETHYL-CARBOXYLIC ACID DERIVATIVES

(75) Inventors: Andreas Boehm, München (DE); Hermann Petersen, Burghausen (DE); Juergen Stohrer, Pullach (DE)

(73) Assignee: Consortium fuer Elektrochemische Industrie GmbH, Munich (DE)

( * ) Notice: Subject to any disclaimer, the term of this patent is extended or adjusted under 35 U.S.C. 154(b) by 0 days.

(21) Appl. No.: 11/288,530

(22) Filed: Nov. 29, 2005

(65) Prior Publication Data

US 2006/0122424 A1 Jun. 8, 2006

(30) Foreign Application Priority Data

Dec. 1, 2004 (DE) ..................... 10 2004 057 995

(51) Int. Cl.
*C07C 229/00* (2006.01)

(52) U.S. Cl. ........................................ 562/567; 556/42

(58) Field of Classification Search ................ 562/567; 556/442

See application file for complete search history.

(56) References Cited

U.S. PATENT DOCUMENTS 3,912,772 A * 10/1975 Pfeffer et al. ............... 554/157
4,837,357 A * 6/1989 Merger et al. .............. 554/150

FOREIGN PATENT DOCUMENTS

DE 692 25 897 T2 10/1998

OTHER PUBLICATIONS

Clive et al., "Synthesis of the Racemic Tetracyclic Core of CP-225,917: Use of a strain-=assisted Cope rearrangement"; Tetrahedron Letters 43 (2002), pp. 4559-4563.

LeFevre et al., "Intramolecular Steric Factors in the Thermolysis of 4-Alkylidene-1-pyrazolines", J. Am. Chem. Soc., 1986, pp. 1019-1027.

Kato et al., "Efficient Synthesis of Some 2- oxaspiro[3,5]Nona-1-Ones As Anisatin Models", Chemistry Letters,1985, pp. 1785-1788.

Baker et al., "The Synthesis of [2.2.2.] Bicylooctaine and [3.1.1]Bicycloheptane Based Amino Acids as Contrained Glutamate Analogues", Tetrahedron Letters 40, (1999), pp. 781-784.

Neustadt et al., "Mercaptoacycl Amino Acid Inhibitors of Atriopepridase. 1.Structure-Activity Relationship Studeis of Methionine and S-Alkylcysteine Derivatives", J. Med. Chem. 1994, 37, pp. 2461-2476.

Pettit et al., "Synthesis of A Spirovetivane Synthon", Synthetic Communications, 11(3), 1981, pp. 167-177.

Ziegler et al., "Formation of 9, 10-Unsaturation in the Mitomycins: Facile Fragmentation of β-Alkyl-β-aryl-α-oxo-γ-butyrolactones", Organic Letters, 2000, vol. 2, No. 23, pp. 3619-3621.

Greene et al., "Protective Groups In Organic Synthesis", John Wiley & Sons, Inc., 3rd Edition.

Derwent Abstract corres. to DE 692 25 897 T2.

Kuwajima et al., "A Convenient Method For The Preparation Of β-Hydroxy Esters", Tetrahedron Letters, No. 26, pp. 2253-2256. 1976.

* cited by examiner

*Primary Examiner*—Thurman K. Page
*Assistant Examiner*—Chukwuma Nwaonicha
(74) *Attorney, Agent, or Firm*—Brooks Kushman P.C.

(57) ABSTRACT

The invention relates to a novel process for hydroxymethylating noncyclic α,α-dialkylcarboxylic acid derivatives with formaldehyde using amide bases at temperatures of from −40° C. up to the boiling point of the solvent or solvent mixture used.

9 Claims, No Drawings

PROCESS FOR PREPARING α, α-DIALKYL-α-HYDROXYMETHYL-CARBOXYLIC ACID DERIVATIVES

BACKGROUND OF THE INVENTION

1. Field of the Invention

The invention relates to a novel process for hydroxymethylating noncyclic α,α-dialkylcarboxylic acid derivatives with formaldehyde using amide bases at temperatures of from −40° C. up to the boiling point of the solvent or solvent mixture used.

The target compounds are suitable as intermediates for preparing polymers and active pharmaceutical ingredients and thus of great industrial and economic interest.

2. Background Art

The prior art discloses a series of processes for hydroxymethylating α,α-dialkylcarboxylic acid derivatives. The general principle of the reactions known from the prior art is the use of formaldehyde as the hydroxymethylating reagent in the presence of a base, predominantly those from the class of the amide bases, at low temperatures. It is known in particular that α,α-dialkylcarboxylic esters, after deprotonation with lithium diisopropylamide (LDA), can be reacted with formaldehyde, to give the corresponding α,α-dialkyl-α-hydroxymethylcarboxylic esters at low temperatures.

Derrick L . J . Clive et al. (Tetrahedron Letters 43 (2002), p. 4559-4563) and Gerard N. LeFevre et al. (Journal of the American Chemical Society 108 (1986), p. 1019-1027) each describe a process for hydroxymethylating a norbornene derivative with paraformaldehyde. Both for the generation of the enolate of the ester used as the starting compound (ester enolate) with LDA and in the further reaction of the thus generated enolate with paraformaldehyde, it is necessary to employ very low temperatures of −78° C. in order to achieve a significant conversion. The product yields are nevertheless only 43% and 61% respectively.

The reaction of structurally closely related cyclohexanoic esters and cyclopentanoic esters with lithium diisopropylamide and gaseous formaldehyde has been described by Michiharu Kato et al. (Chemistry Letters (1985), p. 1785-1788), S. Richard Baker et al. (Tetrahedron Letters 40 (1999), p. 781-784) and B. R. Neustadt et al. (J. Med. Chem. 37 (1994), p. 2461-2467). Both for the generation of the ester enolate with LDA and for the further reaction with formaldehyde, very low temperatures of −78° C. are again also employed in this process.

The conversion of an α,α-dialkylcarboxylic ester at higher temperatures has been achieved only by the use of a very specific and expensive base, since no reaction whatsoever is otherwise observed under non-low-temperature conditions. George R. Pettit et al. (Synthetic Communications 11(3), 1981, p. 167-177) describe the deprotonation of a cyclohexane carboxylic ester with trityllithium and subsequent hydroxymethylation of the enolate formed with paraformaldehyde at ice-bath temperatures. The authors suspected that the formation of the carbanion in this case is particularly difficult and therefore a specific base for deprotonation, such as trityllithium, has to be used.

The hydroxymethylation of a free α,α-dialkylcarboxylic acid by generation of the enolate with an excess of LDA and reaction with gaseous formaldehyde has been described using the example of a cyclohexane carboxylic acid derivative by F. E. Ziegler et al. (Organic Letters 2 (2000), p. 3619-3622). However, in this process too, very low temperatures of −78° C. again have to be employed.

With knowledge of the prior art, the skilled person can thus draw the inference that, for the successful hydroxymethylation of the α,α-dialkylcarboxylic acid derivatives described therein with formaldehyde using amide bases, temperatures of −78° C. are obligatory. When higher reaction temperatures are desired, a reaction can be achieved only when specific and expensive bases are used, for example trityllithium.

For a large-scale or industrial hydroxymethylation reaction of α,α-dialkylcarboxylic acid derivatives, however, both the need to employ low-temperature conditions and/or the use of specific and costly reagents are afflicted with great technical and economic disadvantages.

Moreover, the prior art does not disclose any analogous hydroxymethylation reactions of α,α-dialkylcarboxylic acid derivatives, in which the carbon atom in the α-position to the carboxyl group is not part of a cyclic hydrocarbon system, since the substrates described in the prior art derive exclusively from cyclopentane, cyclohexane or norbornene carboxylic acid derivatives. The hydroxymethylation of α,α-dialkylcarboxylic acid derivatives which do not have this structural feature has not been described to date in the prior art. In particular, the hydroxymethylation of open-chain substrates, for example 2-ethylhexanoic acid and its derivatives, with formaldehyde has not yet been described.

Thus, whether the hydroxymethylation of α,α-dialkylcarboxylic acid derivatives in which the carbon atom α to the carboxyl group is not part of a cyclic hydrocarbon system is possible at all, or whether specific procedures would be required with such substrates, were unknown. Indeed, the prior art suggests that hydroxymethylations are possible exclusively with carboxylic acid derivatives in which the carbon atom α to the carboxyl group is part of a cyclic hydrocarbon system, and even then, the process must take place under low-temperature conditions or with the use of specific reagents.

SUMMARY OF THE INVENTION

It is therefore an object of the invention to provide a process for hydroxymethylating α,α-dialkylcarboxylic acid derivatives, which avoids the problems known from prior art processes. It is a particular object of the invention to provide a process for preparing α,α-dialkyl-α-hydroxymethylcarboxylic acid derivatives starting from α,α-dialkylcarboxylic acid derivatives in which the carbon atom in the α-position to the carboxyl group is not part of a cyclic hydrocarbon system ("cycle" or "ring system").

These and other objects are achieved by a process for preparing α,α-dialkyl-α-hydroxymethylcarboxylic acid derivatives starting from α,α-dialkylcarboxylic acid derivatives, in which the carbon atom in the α-position which is to be subjected to the hydroxymethylation is not part of a cycle, by reacting with formaldehyde in the presence of an amide base at reaction temperatures from −40° C. up to the boiling point of the solvent or solvent mixture used.

DETAILED DESCRIPTION OF THE PREFERRED EMBODIMENT(S)

It has now surprisingly been found that acyclic α,α-dialkylcarboxylic acid substrates can be converted to the α,α-dialkyl-α-hydroxymethylcarboxylic acid target compounds with high yields and purities under these reaction conditions. The process is especially notable in that it is possible to operate with bases common on the industrial scale, in particular amide bases, with comparatively uncomplicated reaction temperatures. It is possible to dispense with the use of specific and expensive bases such as trityllithium and the need to perform the reaction at very low temperatures of −78° C. Moreover, the process for the first time opens up the possibility of also subjecting carboxylic acid derivatives which do not derive from cyclopentane, cyclohexane or norbornene compounds, to a hydroxymethylation with formaldehyde.

The invention therefore provides a process for preparing α,α-dialkyl-α-hydroxymethylcarboxylic acid derivatives or salts thereof of the general formula (II)

Formula (II)

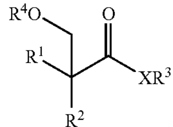

$R^1$ and $R^2$ are each independently selected from among linear or branched alkyl radicals and aralkyl radicals, $R^3$ is selected from among hydrogen, optionally substituted linear or branched alkyl, aryl, aralkyl radicals, silyl radicals, alkali metal, alkaline earth metal and ammonium, $R^4$ is hydrogen, a hydroxyl protecting group, alkali metal or alkaline earth metal, and X is selected from among oxygen, sulfur and $NR^5$, where $R^5$ is in turn selected from among hydrogen, linear or branched alkyl, aryl, aralkyl radicals and silyl radicals, by reacting α,α-dialkylcarboxylic acid derivatives or salts thereof of the general formula (I)

Formula (I)

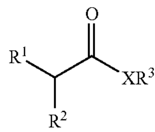

with formaldehyde in the presence of an amide base in one or more solvents, wherein the reaction take place in a temperature range from −40° C. up to the boiling point of the solvent or solvent mixture used.

The inventive process for the first time offers the possibility of hydroxymethylating substrates of the general formula (I) and consequently access to products of the general formula (II) in which the carbon atom at which the hydroxymethylene moiety is introduced is not part of a ring system; in particular, the $R^1$ and $R^2$ radicals in the general formulae (I) and (II) do not form a closed ring system, in particular do not form a hydrocarbon ring, and the $R^1$ and $R^2$ radicals are thus not joined to one another.

The inventive hydroxymethylation of α,α-dialkylcarboxylic acid derivatives or salts thereof of the general formula (I) is carried out in such a way that, in the inventive temperature range, first the reactant of the general formula (I) in a suitable solvent or solvent mixture is deprotonated with an amide base in the position α to the carboxylic acid function, and the reactive intermediate (enolate) thus obtained is subsequently reacted with formaldehyde. Alternatively, the α,α-dialkylcarboxylic acid derivatives or salts thereof of the general formula (I) can also be initially charged together with the formaldehyde and the reaction effected by subsequent addition of the amide base. It is also possible to initially charge the amide base and the formaldehyde and subsequently to add the α,α-dialkylcarboxylic acid derivatives.

Preferred radicals for $R^1$ and $R^2$ are each independently selected from linear or branched alkyl and aralkyl radicals, more preferably methyl, ethyl, n-propyl, isopropyl, n-butyl, isobutyl, tert-butyl, n-pentyl, n-hexyl and benzyl radicals. When $R^3$ is a substituted linear or branched alkyl, aryl, aralkyl radical, such substituents are preferably be selected from among functional groups comprising halogen, cyano and alkoxy, in particular from the group of the halogens. When $R^3$ or $R^5$ are silyl radicals, they are preferably dialkylsilyl or trialkylsilyl radicals, in which case the alkyl radicals present therein may be linear or branched. Preferred radicals for $R^3$ and for $R^5$ are methyl, ethyl, n-propyl, isopropyl, n-butyl, isobutyl, tert-butyl, benzyl and trimethylsilyl radicals.

Preferred salts of the α,α-dialkylcarboxylic acid derivatives of the general formula (I) are those in which $R^3$ is lithium, sodium, potassium, magnesium, calcium or tetraalkylammonium.

Direct process products are the anionic, α-oxymethylene-functionalized target products (alkoxides) of the general formula (II) which derive from the α,α-dialkylcarboxylic acid derivatives or salts thereof of the general formula (I), where $R^4$ is initially the cation stemming from the amide base used, in particular lithium or sodium, and is obtained by aqueous workup of a hydroxyl functionality in which $R^4$ is hydrogen.

It is also possible to react the hydroxymethyl compounds further with reagents for introducing hydroxylprotecting groups or leading groups, in particular, to further functionalize or derivatize them with acyl, silyl, benzyl, mesyl or tosyl groups. $R^4$ may accordingly quite generally be any alcohol protecting group (hydroxyl protecting group) useful for this purpose. Many of such protecting groups are known to those skilled in the art. This functionalization or derivatization can also be effected in the course of workup of the direct process products by processes customary in organic synthesis and known to those skilled in the art, without preceding conversion to, or isolation of, the hydroxymethyl compound.

Preferred hydroxyl protecting groups for $R^4$ are optionally substituted linear or branched alkyl, acyl, aryl or aralkyl radicals and silyl radicals, in particular dialkylsilyl radicals and trialkylsilyl radicals. When $R^4$ is a substituted linear or branched alkyl, aryl, or aralkyl radical, preference is given to halogen, cyano and alkoxy functional group substituents, in particular to halogen substituents.

When $R^4$ is a dialkylsilyl or trialkylsilyl radical, the alkyl radicals present therein may be linear or branched. Preferred silyl radicals $R^4$ are trialkylsilyl radicals having from 3 to 12 carbon atoms, in particular the trimethylsilyl radical.

Specific, particularly preferred embodiments of hydroxyl protecting groups for $R^4$ are acetyl, trimethylsilyl, benzyl, mesyl or tosyl radicals.

In a particular embodiment of the process, the direct process products formed in the reaction (primary products) are derivatized before the further, generally aqueous/organic, workup. Thus, the alkoxides and/or in some cases also carboxylates of the general formula (II) which are initially present in the reaction mixture may be derivatized or functionalized directly after the reaction by adding suitable reagents.

For derivatization or functionalization, all protecting groups useful for protecting alcohols and carboxylic acids are suitable, in particular the groups known from Protective Groups in Organic Synthesis, 3rd Edition, editors T. W. Greene and P. G. M. Wuts, John Wiley & Sons, Inc. 1999.

The alkoxides and/or in some cases also the carboxylates of the formula (II) which are initially present in the reaction mixture are preferably derivatized directly after the reaction by adding chlorosilanes, mesyl chloride, tosyl chloride, benzyl chloride or benzyl bromide. Particular preference is given to using trimethylchlorosilane and dichlorodimethylsilane. The derivatization may of course also be carried out with the correspondingly protonated alcohols and carboxylic acids in which $R^3$ and/or $R^4$ is hydrogen.

The preferred reactants of the general formula (I) are α,α-dialkylcarboxylic esters and the free α,α-dialkylcarboxylic acids or salts thereof, where X is oxygen (O) and $R^3$ is hydrogen, or an optionally substituted linear or branched alkyl, aryl, aralkyl radical or silyl radical, in particular, a hydrogen, methyl, ethyl, n-propyl, isopropyl, n-butyl, isobutyl, tert-butyl, benzyl and trimethylsilyl radical.

When the aforementioned α,α-dialkylcarboxylic esters or the free α,α-dialkylcarboxylic acids are used as reactants and $R^3$ is a silyl radical, this silyl radical is preferably a dialkylsilyl or trialkylsilyl radical, where the alkyl radicals herein may be linear or branched.

In addition to the free α,α-dialkylcarboxylic acids, preferred reactants of the general formula (I) are also their salts in which X is oxygen (O) and $R^3$ is an alkali metal, alkaline earth metal, or ammonium, in particular, lithium, sodium, potassium, magnesium, calcium, or tetraalkylammonium.

Particularly preferred reactants of the general formula (I) are α,α-dialkylcarboxylic esters where X is oxygen (O) and $R^3$ is an optionally substituted linear or branched alkyl, aryl, aralkyl or silyl radical. Particular preference is given to $R^3$ being a methyl, ethyl, n-propyl, isopropyl, n-butyl, isobutyl, tert-butyl, benzyl, or trimethylsilyl radical. Among these particularly preferred reactants, particular preference is given to those in which both the $R^1$ and $R^2$ radicals are selected the radicals listed above.

The salts of the α,α-dialkylcarboxylic acids may either be used directly in the reaction or else be prepared in a simple manner in situ from the corresponding carboxylic acids by addition of a suitable base. Suitable bases for this purpose are, for example metal hydroxides, amides, carbonates, hydrogencarbonates, and hydrides. The bases used for this purpose are more preferably sodium hydride, lithium hydride, sodium hydroxide and lithium hydroxide. Any water of reaction formed can be removed from the reaction mixture before the enolate is generated, for example, by azeotropic distillation using a suitable solvent, for example toluene, pentane, MTBE and methylene chloride.

In a particularly simple embodiment of the hydroxymethylation of α,α-dialkylcarboxylic acids, an amide base is used both to deprotonate the carboxylic acid function —COOH and to generate the enolate. Accordingly, at least 2 equivalents of the amide base used are needed for double deprotonation.

Suitable amide bases are in principle all metal amides which are known from the prior art to those skilled in the art and are typically used in organic synthesis. Preferred metal amides are of the general formula (III)

$$M(NR^6R^7)_n \quad \text{Formula (III)}$$

where

M is selected from the group consisting of lithium, sodium, potassium, magnesium and calcium and $R^6$ and $R^7$ are each independently a hydrogen, linear or branched alkyl, aryl, aralkyl, or silyl radical, and n, depending on the valency of M, is 1 or 2.

If $R^6$ and $R^7$ are each independently one or more silyl radicals, they are preferably trialkylsilyl radicals, in which case the alkyl radicals present therein may be linear or branched.

$R^6$ and $R^7$ are preferably each independently selected from the group consisting of methyl, ethyl, n-propyl, isopropyl, n-butyl, isobutyl, tert-butyl, benzyl and trimethylsilyl.

The amide bases used are more preferably sodium hexamethyldisilazide, lithium hexamethyldisilazide, lithium diisopropylamide and lithium tetramethylpiperidine. The amide base used is most preferably lithium diisopropylamide.

Preference is given to using from 0.5 to 10 equivalents, and particular preference to using 1-3 equivalents of the amide base, based on the α,α-dialkylcarboxylic acid derivatives. It should be noted that when the free α,α-dialkylcarboxylic acids are used, an additional equivalent of base is initially consumed for the deprotonation of the COOH group. Alternatively, the COOH group can initially also be deprotonated with alternative bases, as described previously.

Formaldehyde as the reagent for hydroxymethylation can in principle be used in all conceivable forms customary in organic synthesis, in particular as free gaseous formaldehyde, paraformaldehyde, or else as trioxane.

When free gaseous formaldehyde is used, it is preferably generated by depolymerization, for example of paraformaldehyde, at high temperatures of T >150° C., as is known, for example, from B. R. Neustadt et al., J. Med. Chem. 37 (1994), p. 2461-2467. This process, however, constitutes significant additional process complexity. The handling of toxic formaldehyde gas is also problematic for safety reasons. Preference is therefore given to using paraformaldehyde or trioxane, and particular preference to using paraformaldehyde, since distinctly poorer yields of the products are frequently obtained when trioxane is used. Different qualities and different mean chain lengths of the industrially and inexpensively available paraformaldehyde may be used.

Preference is given to using 0.5-10 equivalents of formaldehyde based on the α,α-dialkylcarboxylic acid derivative, more preferably to using 1-5 equivalents and most preferably to using 1-3 equivalents.

For the process according to the invention, preference is given to using a solvent selected from among tetrahydrofuran, diethyl ether, MTBE, dibutyl ether, toluene, methylene chloride, pentane, hexane, heptane and petroleum ether, and also mixtures thereof. Particular preference is given to using tetrahydrofuran, MTBE, dibutyl ether, pentane, hexane or heptane, and also mixtures thereof, with great preference given to using tetrahydrofuran, and mixtures thereof with pentane, hexane and/or heptane.

The inventive hydroxymethylation of α,α-dialkylcarboxylic acids derivatives of the general formula (I) and their salts is generally carried out at temperatures of from T=−40° C. up to the boiling point of the solvent or solvent mixture used. These temperatures can be realized without any great technical complexity or economic cost. Low-temperature conditions, as have been described in the prior art for the reaction of α,α-dialkylcarboxylic acid derivatives with formaldehyde using amide bases (T=−78° C.), signify, in comparison thereto, a distinctly higher level of process complexity and thus higher cost.

Particular preference is given to carrying out the hydroxymethylation of α,α-dialkylcarboxylic acid derivatives of the general formula (I) and salts thereof at reaction temperatures of from −30° C. to +60° C. This means a considerable advantage for the economic viability of the process according to the invention. It is particularly surprising that very good yields (up to >90%) and high purities of the products can be obtained in the case of performance in the inventive temperature range.

As products of the hydroxymethylation of α,α-dialkylcarboxylic acid derivatives and salts thereof of the general formula (I), α,α-dialkyl-α-hydroxymethylcarboxylic acid derivatives or salts thereof of the general formula (II) are obtained.

Formula (II)

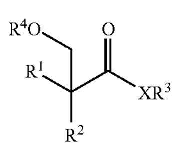

where the $R^1$, $R^2$, $R^3$, $R^4$, $R^5$ and X radicals are each as defined above, each of these radicals in particular being selected from the abovementioned preferred embodiments.

In particular, it is possible by the process to obtain 2-ethyl-2-hydroxymethylhexanoic acid from 2-ethylhexanoic acid and methyl 2-ethyl-2-hydroxymethylhexanoate from methyl 2-ethylhexanoate (see examples).

The following examples serve to illustrate the invention in a detailed manner and should not be interpreted as restricting the invention in any way.

EXAMPLES

Example 1 methyl-2-ethyl-2-hydroxymethylhexanoate 47 ml (0.334 mol) of diisopropylamine are added dropwise at 20° C. to a solution of 118 ml (0.319 mol) of n-butyllithium (2.7 M in heptane) in 118 ml of THF, and the mixture is stirred at 20° C. for 30 min. Within approx. 15 min, 48 g (0.304 mol) of methyl 2-ethylhexanoate are added dropwise at −20° C., and the mixture is stirred at −20° C. for 30 min and subsequently admixed with 27 g (0.90 mol) of paraformaldehyde. After 30 min at −20° C., the mixture is stirred at 0° C. for a further 2 h. After the solvent has been removed at 20° C. and 20 mbar (approx. 250 ml), 100 ml of MTBE and 200 ml of saturated aqueous solution of ammonium chloride are added to the oily residue and the mixture is stirred at RT for 2 h. The organic phase is removed, the aqueous phase is re-extracted 1× with 100 ml of MTBE and the combined organic phases are concentrated on a rotary evaporator. The crude product (97% conversion based on methyl 2-ethylhexanoate) can be purified by distillation to obtain methyl 2-ethyl-2-hydroxymethylhexanoate (b.p.: 100° C., 6 mbar) in 91% yield with a purity of >99%.

Example 2 methyl-2-ethyl-2-hydroxymethylhexanoate 5.2 ml (0.037 mol) of diisopropylamine are added dropwise at 0° C. to a solution of 12.9 ml (0.035 mol) of n-butyllithium (2.7 M in heptane) in 17 ml of THF, and the mixture is stirred at 0° C. for 15 min. Within approx. 10 min, 5 g (0.032 mol) of methyl 2-ethylhexanoate are added dropwise at 0° C., and the mixture is stirred at 0° C. for 30 min and subsequently admixed with 2.9 g (0.097 mol) of paraformaldehyde. After stirring at 0° C for 2 hours, a saturated aqueous solution of ammonium chloride (20 ml) is added and the mixture is stirred at RT for 2 h. The organic phase is removed, the aqueous phase is re-extracted once with 20 ml of MTBE and the combined organic phases are concentrated on a rotary evaporator. The yield of pure product is 83% (GC).

Example 3 methyl-2-ethyl-2-hydroxymethylhexanoate 5.2 ml (0.037 mol) of diisopropylamine are added dropwise at 20° C. to a solution of 12.9 ml (0.035 mol) of n-butyllithium (2.7 M in heptane) in 17 ml of THF, and the mixture is stirred at 20° C. for 15 min. Within approx. 10 min, 5 g (0.032 mol) of methyl 2-ethylhexanoate are added dropwise at 20° C., and the mixture is stirred at 20° C. for a further 30 min and subsequently admixed with 2.9 g (0.097 mol) of paraformaldehyde. After stirring at 20° C. for 2 hours, a saturated aqueous solution of ammonium chloride (20 ml) is added and the mixture is stirred at RT for 2 h. The organic phase is removed, the aqueous phase is re-extracted 1× with 20 ml of MTBE and the combined organic phases are concentrated on a rotary evaporator. The yield of pure product is 77% (GC).

Example 4 methyl-2-ethyl-2-hydroxymethylhexanoate 9.8 ml (0.070 mol) of diisopropylamine are added dropwise at 20° C. to a solution of 24.4 ml (0.065 mol) of n-butyllithium (2.7 M in heptane) in 25 ml of MTBE, and the mixture is stirred at −20° C. for 30 min. Within approx. 10 min, 10 g (0.063 mol) of methyl 2-ethylhexanoate are added dropwise at −20° C., and the mixture is stirred at 20° C. for a further 30 min and subsequently admixed with 5.7 g (0.19 mol) of paraformaldehyde. After 30 min at −20° C., the mixture is stirred at 0° C. for 2 h. After the removal of the solvent at 20° C. and 20 mbar, 20 ml of MTBE and 40 ml of saturated aqueous solution of ammonium chloride are added to the oily residue (approx. 20 g) and the mixture is stirred at RT for 2 h. The organic phase is removed, the aqueous phase is re-extracted 1× with 20 ml of MTBE and the combined organic phases are concentrated on a rotary evaporator. The yield of pure product is 86% (GC).

Example 5 methyl-2-ethyl-2-hydroxymethylhexanoate 47 ml (0.334 mol) of diisopropylamine are added dropwise at −20° C. to a solution of 118 ml (0.319 mol) of n-butyllithium (2.7 M in heptane) in 118 ml of THF, and the mixture is stirred at −20° C. for 30 min. Within approx. 15 min, 48 g (0.304 mol) of methyl 2-ethylhexanoate are added dropwise at −20° C., and the mixture is stirred at −20° C. for a further 30 min and subsequently admixed with 18 g (0.60 mol) of paraformaldehyde. After 30 min at −20° C., the mixture is stirred at 0° C. for 2 h. After addition of 100 ml of MTBE and 100 ml of saturated aqueous solution of ammonium chloride, the mixture is stirred at RT for 2 h. The organic phase is removed, the aqueous phase is re-extracted 1×with 100 ml of MTBE and the combined organic phases are concentrated on a rotary evaporator. The crude product (97% conversion based on methyl 2-ethylhexanoate) can be purified by distillation to obtain methyl 2-ethyl-2-hydroxymethylhexanoate (b.p.: 100° C., 6 mbar) in 91% yield with a purity of >99%.

Example 6

2-ethyl-2-hydroxymethylhexanoic acid 27 ml (72.9 mmol) of n-butyllithium (2.7 M in heptane) are added dropwise at 0° C. to a solution of 10.9 ml of diisopropylamine (77.5 mmol) in 60 ml of THF, and the mixture is stirred at 0° C. for 30 min. Within 10 min, 5 g (34.7 mmol) of 2-ethylhexanoic acid are added dropwise at 0° C. and the reaction mixture is heated at 50° C. for 1.5 h. The clear solution is cooled to −20° C. and admixed with 3.1 g (103 mmol) of paraformaldehyde. After 10 min at −20° C., the mixture is stirred at RT for 2 h. The mixture is admixed with saturated aqueous solution of ammonium chloride and adjusted to pH=1-2 with 6N HCl. The organic phase is removed, the aqueous phase is re-extracted once with MTBE and the combined organic phases are concentrated on a rotary evaporator. The crude product (85% yield (GC)) can be purified further by distillation (b.p.: 121° C., 0.2 mbar). Alternatively, it is also possible to crystallize the sodium salt of the product from aqueous solution in pure form. The pure product of the free 2-ethyl-2-hydroxymethylhexanoic acid, which is typically obtained as a viscous oil, crystallizes slowly at RT (melting point: 45-46° C.). Alternatively, the product can also be crystallized from a suitable solvent, for example pentane, hexane, heptane or petroleum ether.

Example 7

2-ethyl-2-hydroxymethylhexanoic acid 27 ml (72.9 mmol) of n butyllithium (2.7 M in heptane) are added dropwise at 0° C. to a solution of 10.9 ml of diisopropylamine (77.5 mmol) in 60 ml of THF, and the mixture is stirred at 0° C. for 30 min. Within 10 min, 5 g (34.7 mmol) of 2-ethylhexanoic acid are added dropwise at 0° C. and the reaction mixture is heated to 50° C. for 1.5 h. The clear solution is cooled to 0° C. and admixed with 3.1 g (103 mmol) of paraformaldehyde. After 10 min at 0° C., the mixture is stirred at RT for 18 h. The mixture is admixed with saturated aqueous solution of ammonium chloride and adjusted to pH=1-2 with 6N of HCl. The organic phase is removed, the aqueous phase is re-extracted once with MTBE and the combined organic phases are concentrated on a rotary evaporator. The yield of pure product is 89% (GC).

Example 8

2-ethyl-2-hydroxymethylhexanoic acid 113 ml (0.305 mol) of n-butyllithium (2.7 M in heptane) are added dropwise at 0° C. to a solution of 46 ml of disiopropylamine (0.327 mol) in 320 ml of THF and the mixture is stirred at 0° C. for 30 min (Solution 1). 40 g (0.277 mol) of 2-ethylhexanoic acid are added dropwise at 25° to a suspension of 7 g of NaH 95% (0.277 mol) in 320 ml of THF within approx. 15 min, and the reaction mixture is stirred at 50° C. for 30 min (Solution 2). Solution 1 is added at 0° C. to Solution 2 and subsequently heated to 50° C. for 1.5 h. The clear solution is cooled to 0° C. and admixed with 25 g (0.833 mol) of paraformaldehyde. After 10 min, the mixture is stirred at RT for 18 h. The mixture is admixed with saturated aqueous solution of ammonium chloride and adjusted to pH=1-2 with 6N HCl. The organic phase is removed, the aqueous phase is re-extracted 1× with MTBE and the combined organic phases are concentrated on a rotary evaporator. The yield of pure product is 71% (GC).

Example 9

2-ethyl-2-hydroxymethylhexanoic acid 113 ml (0.305 mol) of n-butyllithium (2.7 M in heptane) are added dropwise at 0° C. to a solution of 46 ml of dissopropylamine (0.327 mol) in 320 ml of THF and the mixture is stirred at 0° C. for 30 min (Solution 1). 40 g (0.277 mol) of 2-ethylhexanoic acid are added dropwise at 25° C. to a suspension of 7 g of NaH 95% (0.277 mol) in 320 ml of THF within approx. 15 min, and the reaction mixture is stirred at 50° C. for 30 min (Solution 2). Solution 1 is added at 0° C. to Solution 2 and subsequently heated to 50° C. for 1.5 h. The clear solution is cooled to −20° C. and admixed with 25 g (0.833 mol) of paraformaldehyde. After 10 min, the mixture is stirred at RT for 18 h. The mixture is admixed with saturated aqueous solution of ammonium chloride and adjusted to pH=1-2 with 6N HCl. The organic phase is removed, the aqueous phase is re-extracted once with MTBE and the combined organic phases are concentrated on a rotary evaporator. The yield of pure product is 70% (GC).

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A process for preparing α,α-dialkyl-α-hydroxymethylcarboxylic acid derivatives or salts thereof of the formula (II)

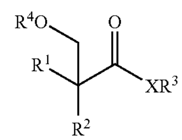

(II)

where $R^1$ and $R^2$ are each independently selected from the group consisting of linear and branched alkyl radicals and aralkyl radicals, $R^3$ is selected from the group consisting of hydrogen, optionally substituted linear and branched alkyl, aryl, aralkyl radicals, silyl radicals, alkali metal, alkaline earth metal, and amimonium, $R^4$ is hydrogen, a hydroxyl protecting group, alkali metal or alkaline earth metal, X is oxygen, where $R^5$ is selected from the group consisting of hydrogen, linear or branched alkyl, aryl, aralkyl radicals and silyl radicals, comprising: reacting α,α-dialkylcarboxylic acid derivatives or salts thereof of the formula (I)

(I)

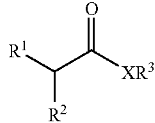

with paraformaldehyde in the presence of an amide base in a solvent or solvent mixture at a reaction temperature of from −40° C. up to the boiling point of the solvent or solvent mixture.

2. The process of claim 1, wherein the α,α-dialkylcarboxylic esters or α,α-dialkylcaiboxylic acids or salts thereof are compounds of the formula (I) where X is oxygen (O) and $R^3$ is selected from the group consisting of linear and branched alkyl, aryl, aralkyl, and silyl radicals.

3. The process of claim 2, wherein X is oxygen (O) and $R^3$ is selected from the group consisting of methyl, ethyl, n-propyl, isopropyl, n-butyl, isobutyl, tert-butyl, benzyl and trimethylsilyl.

4. The process of claim 1, wherein from 1 to 3 equivalents of the amide base based on α,α-dialkylcarboxylic acid derivative or salt thereof are used.

5. The process of claim 1, wherein the solvent is selected from the group consisting of tetrahydrofuran, diethyl ether, MTBE, dibutyl ether, toluene, methylene chloride, pentane, hexane, heptane, petroleum ether, and mixtures thereof.

6. The process of claim 1, wherein the amide base is a metal amide of the formula (III)

$$M(NR^6R^7)_n \quad \text{(III)}$$

where

M is selected from the group consisting of lithium, sodium, potassium, magnesium and calcium, $R^6$ and $R^7$ are each independently selected from the group consisting of hydrogen, linear and branched alkyl, aryl, aralkyl, and silyl radicals, and n, depending on the valency of M, is 1 or 2.

7. The process of claim 1, wherein the amide base is sodium hexamethyldisilazide, lithium hexamethyldisilazide, lithium diisopropylamide, or lithium tetramethylpiperidine.

8. The process of claim 1, wherein the reaction is carried out at a temperature of from −30° C. to +60° C.

9. A process for preparing α,α-dialkyl-α-hydroxymethylcarboxylic acid derivatives of the formula (II)

(II)

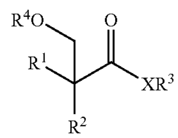

where $R^1$ and $R^2$ are each independently selected from the group consisting of linear and branched alkyl radicals and aralkyl radicals, $R^3$ is selected from the group consisting of optionally substituted linear and branched alkyl radicals, aryl radicals, aralkyl radicals, and silyl radicals, $R^4$ is hydrogen, a hydroxyl protecting group, alkali metal or alkaline earth metal, X is oxygen, where $R^5$ is selected from the group consisting of hydrogen, linear or branched alkyl, aryl, aralkyl radicals and silyl radicals, comprising: reacting α,α-dialkylcarboxylic acid derivatives of the formula (I)

(I)

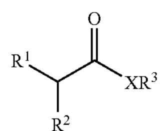

with paraformaldehyde in the presence of an amide base in a solvent or solvent mixture at a reaction temperature of from −40° C. up to the boiling point of the solvent or solvent mixture.

* * * * *